United States Patent [19]

Vora

[11] Patent Number: 4,523,048
[45] Date of Patent: Jun. 11, 1985

[54] PROCESS FOR THE SELECTIVE PRODUCTION OF ALKYLBENZENES

[75] Inventor: Bipin V. Vora, Elk Grove Village, Ill.

[73] Assignee: UOP Inc., Des Plaines, Ill.

[21] Appl. No.: 596,772

[22] Filed: Apr. 4, 1984

[51] Int. Cl.³ .................................................. C07C 1/00
[52] U.S. Cl. ..................................... 585/323; 585/455; 585/456
[58] Field of Search ........................ 585/323, 455, 456

[56] References Cited

U.S. PATENT DOCUMENTS

| | | | |
|---|---|---|---|
| 3,234,298 | 2/1966 | van Zijll Langhout et al. | 585/274 |
| 3,472,763 | 10/1969 | Cosyns et al. | 208/255 |
| 3,484,498 | 12/1969 | Berg | 585/315 |
| 3,494,971 | 2/1970 | Fenske | 585/491 |
| 3,655,621 | 4/1972 | Kasperik et al. | 585/262 |
| 3,662,015 | 5/1972 | Komatsu et al. | 585/261 |
| 3,696,160 | 10/1972 | Chomyn | 585/262 |
| 4,409,401 | 10/1983 | Murtha | 568/362 |
| 4,409,410 | 10/1983 | Cosyns et al. | 585/259 |

Primary Examiner—Curtis R. Davis
Attorney, Agent, or Firm—William H. Page, II; John F. Spears, Jr.

[57] ABSTRACT

An improved process for the production of alkylaromatic hydrocarbons is disclosed. Paraffinic hydrocarbons are dehydrogenated to yield an olefin-containing stream, which is later charged to an alkylation zone for reaction with an aromatic hydrocarbon. The olefin-containing stream is first passed through a selective hydrogenation zone in which diolefins are converted to monoolefins by contact with a selective catalyst. This increases the yield and the quality of the product alkylate by greatly reducing the production of biphenyl compounds and oligomers in the alkylation zone. The selective hydrogenation zone is located between the vapor-liquid separator and stripper column of the dehydrogenation zone.

14 Claims, 1 Drawing Figure

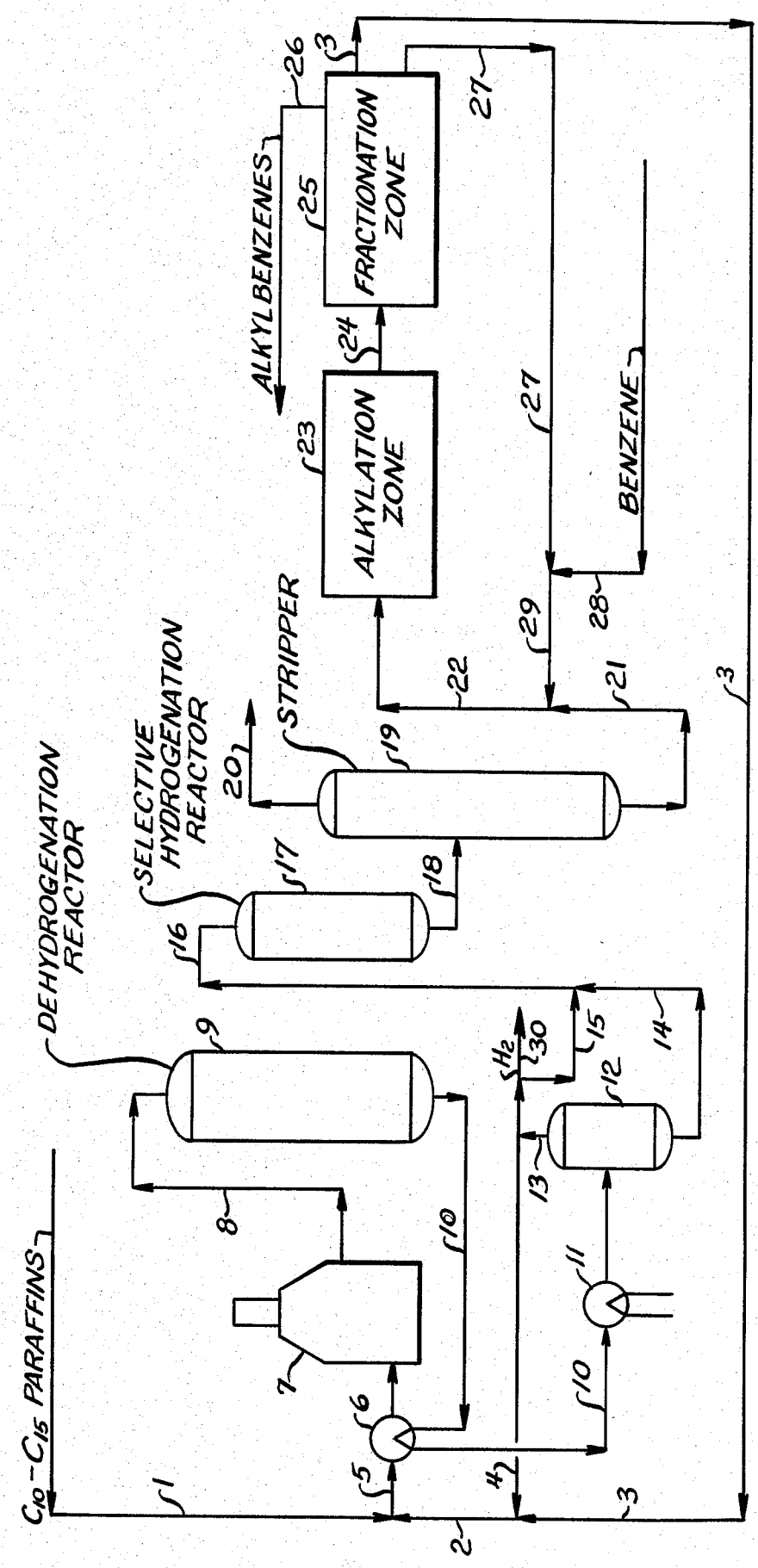

PROCESS FOR THE SELECTIVE PRODUCTION OF ALKYLBENZENES

FIELD OF THE INVENTION

The invention relates to the broad field of hydrocarbon processing. The invention may also be broadly classified as relating to a process for the production of alkylaromatic hydrocarbons. More specifically, the invention relates to an integrated hydrocarbon conversion process in which dehydrogenation, selective hydrogenation, and alkylation reactions are performed. The invention is directly concerned with the reduction in by-product formation and an improvement in alkylate product in the alkylation zone of this integrated process. This improvement is achieved through the selective hydrogenation of diolefins present in the dehydrogenation reactor effluent stream to monoolefins. The invention is specifically directed to the integration of the selective hydrogenation reactor into the process.

INFORMATION DISCLOSURE

The production of alkylaromatic hydrocarbons by the combined steps of paraffin dehydrogenation and aromatic alkylation using the resultant olefinic hydrocarbons is an established commercial process. The overall flow schemes of processes corresponding to the general preferred flow of the subject process are illustrated in U.S. Pat. No. 3,484,498 issued to R. C. Berg and U.S. Pat. No. 3,494,971 issued to E. R. Fenske. The former reference illustrates the passage of a normal paraffin charge stream into a dehydrogenation zone, with the effluent of this zone passing through a condenser not shown in which the vapor phase reactor effluent is partially condensed. The resultant mixed phase material is passed into a separating zone in which it is separated into a hydrogen-rich recycle stream and a liquid phase process stream. The liquid phase process stream is passed through a stripping zone which preferably comprises a trayed fractionation column. Hydrocarbons which remain after stripping off the light hydrocarbons are passed into an alkylation zone in admixture with benzene or other aromatic hydrocarbons. Hydrogen fluoride is the preferred alkylation catalyst. The effluent of the alkylation zone is passed into a fractionation system which produces several effluent streams including a product stream and a normal paraffin recycle stream which is directed into the dehydrogenation zone. The Fenske reference also illustrates the combination of a dehydrogenation zone with an alkylation zone, but supplies further details as to a preferred arrangement of the alkylation zone. These references also describe functional dehydrogenation catalysts and conditions.

U.S. Pat. No. 3,696,160 issued to K. D. Chomyn is pertinent for its teaching that those skilled in the art of hydrocarbon processing are aware that it aay be beneficial to selectively hydrogenate diolefins to monoolefins in certain hydrocarbon streams. This reference is directed to the selective conversion of propadiene and butadiene contaminants in propylene and butene charge stocks employed in alkylation processes for the production of aviation and aotor fuel. In this alkylation process, a $C_3$–$C_4$ feed stream is converted to a high octane $C_7$–$C_8$ product. It is stated that a small diolefin content in the alkylation feed stream is undesirable because of increased acid consumption as a result of forming tarry acid-diolefin condensation products, which decreases the profitability of the process. The reference indicates that supported nickel and palladium catalysts are excellent hydrogenation catalysts in the diolefin conversion service, but that their tendency to deactivate in sulfur-containing feedstocks limits their utilization. The reference discloses the use of a sulfided nickel-tungsten catalyst.

U.S. Pat. No. 3,655,621 issued to A. S. Kasperik et al illustrates a process for the selective hydrogenation of $C_4$ diolefins in an alkylation feed stream employing a catalyst comprising presulfided nickel supported on a refractory base. In U.S. Pat. No. 3,234,298 issued to W. C. van Zijll Langhout et al, a process is disclosed for the selective hydrogenation of light, diene-containing cracked hydrocarbon oils. This process is employed to increase the stability of such materials as pyrolysis gasoline and kerosene obtained by severe thermal cracking operations. Such hydrogenation is desirable to reduce the gum-forming characteristics and other undesirable properties of these hydrocarbon mixtures. The process is described as being applicable to diene-containing hydrocarbons ranging from $C_3$ to $C_{18}$ in carbon number. The process employs a catalyst comprising sulfided nickel on alumina or sulfided molybdenum on alumina.

U.S. Pat. No. 3,472,763 issued to J. Cosyns et al is pertinent for its description of a selective diolefin hydrogenation catalyst which comprises nickel supported on an alumina substrate having a number of specified characteristics and for its teaching of the utility of this catalyst. Specifically, it is taught that this catalyst may be employed for the conversion of all types of conjugated diolefins to monoolefins and in particular to the conversion of aliphatic conjugated diolefins having up to 15 carbon atoms per molecule to the corresponding monoolefins. The invention is also described as being useful in the selective hydrogenation of alpha alkenyl aromatic hydrocarbons to the corresponding alkylaromatic hydrocarbons. Another application of the process is the selective hydrogenation of gasolines containing diolefins and other gum-forming hydrocarbons.

The use of catalysts which comprise palladium supported on a refractory material is described in U.S. Pat. No. 3,662,015 issued to Y. Komatsu et al; U.S. Pat. No. 4,409,401 issued to T. P. Murtha; and U.S. Pat. No. 4,409,410 issued to J. Cosyns et al.

BRIEF SUMMARY OF THE INVENTION

The invention provides an improved process for the production of alkylaromatic hydrocarbons by eliminating or at least substantially reducing the concentration in the alkylation zone effluent stream of undesirable by-products including biphenyl compounds, indanes, and tetralins. Besides increasing the purity of the desired monoalkylated benzenes, the subject process also increases the yield of these desired compounds. These improved results are obtained through the use of a selective hydrogenation reactor placed at a unique location within the overall dehydrogenation zone. The selective hydrogenation zone is located between the product separator and the product stripper. The subject invention is therefore an integrated process rather than a separate feed pretreatment step. This arrangement requires only a very minimal increase in the complexity and capital costs of the process to achieve a greatly significant improvement in operational performance.

One broad embodiment of the invention may be characterized as a process for the production of alkylaromatic hydrocarbons which comprises the steps of passing a paraffin feed stream comprising at least one $C_8$-plus paraffinic hydrocarbon through a dehydrogenation reaction zone maintained at dehydrogenation conditions and thereby producing a vapor phase dehydrogenation reactor effluent stream which comprises $C_8$-plus paraffinic hydrocarbons, $C_8$-plus mono- and diolefinic hydrocarbons, hydrogen, and $C_1$–$C_7$ hydrocarbons; cooling and partially condensing the dehydrogenation reactor effluent stream and separating the dehydrogenation reactor effluent stream in a vapor-liquid separation zone into a vapor phase process stream which comprises hydrogen and a liquid phase process stream which comprises dissolved hydrogen, $C_1$–$C_7$ hydrocarbons, $C_8$-plus paraffinic hydrocarbons, and $C_8$-plus mono- and diolefinic hydrocarbons; passing the liquid phase process stream through a selective hydrogenation reaction zone which contains a selective hydrogenation catalyst and is maintained at diolefin selective hydrogenation conditions and forming a selective hydrogenation reaction zone effluent stream which comprises $C_8$-plus monoolefinic hydrocarbons and is substantially free of $C_8$-plus diolefinic hydrocarbons; passing the selective hydrogenation reaction zone effluent stream into a stripping column operated at conditions which separate substantially all hydrogen and light hydrocarbons from the hydrogenation zone effluent stream and producing a stripping column effluent stream which comprises $C_8$-plus paraffinic hydrocarbons and $C_8$-plus monoolefinic hydrocarbons; passing the stripping zone effluent stream into an alkylation zone maintained at alkylation-promoting conditions which include the presence of an aromatic hydrocarbon and an alkylation catalyst and producing an alkylation zone effluent stream which comprises an alkylaromatic hydrocarbon; and recovering the alkylaromatic hydrocarbon from the alkylation zone effluent stream.

DESCRIPTION OF THE DRAWING

The drawing is a simplified process flow diagram of a preferred embodiment of the invention.

Referring now to the drawing, a paraffin feed stream comprising an admixture of $C_{10}$–$C_{15}$ normal paraffins enters the process through line 1. This feed stream is admixed with hydrogen and other normal paraffins from line 2 and passed through line 5. A mixture of paraffins and hydrogen flowing through line 5 is first heated in the indirect heat exchanger 6 and is then passed into a fired heater 7. The resultant vapor phase mixture of paraffins and hydrogen is passed through line 8 into a dehydrogenation reactor 9. Inside the reactor 9, the paraffins are contacted with a dehydrogenation catalyst at conditions which affect the conversion of a significant amount of the paraffins to the corresponding olefins. There is thus produced a reactor effluent stream carried by line 10 which comprises a mixture of hydrogen, unconverted paraffins, $C_{10}$–$C_{15}$ monoolefins, and a smaller amount of $C_{10}$–$C_{15}$ diolefins and $C_1$–$C_9$ hydrocarbons produced as undesired by-products of the dehydrogenation reaction. This reactor effluent stream is first cooled by indirect heat exchange in the feed-product heat exchanger 6 and is then further cooled in the indirect heat exchange means 11. This cooling is sufficient to condense substantially all of the $C_{10}$-plus hydrocarbons into a liquid phase process stream which separates from the remaining vapor, which is rich in hydrogen. This mixed phase stream enters the vapor-liquid separation vessel 12 wherein it is divided into a hydrogen-rich vapor phase stream removed through line 13 and a liquid phase process stream removed through line 14. The vapor phase stream is divided into a net hydrogen product stream removed through line 30 and a hydrogen recycle stream carried by line 4.

The liquid phase process stream removed from the bottom of the separator 12 contains unconverted $C_{10}$–$C_{15}$ paraffins, $C_{10}$–$C_{15}$ mono- and diolefins, lighter hydrocarbons produced as reaction by-products, and some dissolved hydrogen. A controlled volume of hydrogen from line 15 is admixed into the liquid process stream. It is then passed through line 16 into a selective hydrogenation reactor 17. In this reactor, the liquid phase hydrocarbons and hydrogen are contacted with a catalyst under conditions which promote the selective hydrogenation of diolefins to monoolefins. The liquid phase portion effluent of the selective hydrogenation reactor is then passed through line 18 to a stripper column 19. In this column, the light hydrocarbons produced in the dehydrogenation reactor as by-products and any remaining unconsumed hydrogen are separated from the $C_{10}$-plus hydrocarbons and concentrated into a net overhead stream removed from the process through line 20.

The remainder of the hydrocarbons entering the stripper are concentrated into a net bottoms stream carried by line 21. This stream comprises an admixture of $C_{10}$–$C_{15}$ paraffins and monoolefins and has a greatly reduced concentration of diolefins compared to the dehydrogenation reactor effluent. This admixture is combined with benzene from line 29 and passed into an alkylation zone 23 through line 22. In the alkylation zone, the benzene and olefinic hydrocarbons are admixed in the presence of an alkylation catalyst at alkylation-promoting conditions. The alkylation zone effluent stream carried by line 24 is passed into the fractionation zone 25. This stream comprises an admixture of unreacted benzene, $C_{10}$–$C_{15}$ paraffins, and the product alkylbenzenes. These compounds are separated into a paraffin recycle stream carried by line 3, a benzene recycle stream carried by line 27, and an alkylbenzene product stream carried by line 26. Benzene consumed in the process is charged through line 28.

DETAILED DESCRIPTION

The production of alkylaromatic hydrocarbons by the sequential steps of paraffin dehydrogenation followed by an alkylation reaction is a well established commercial process. The product alkylaromatic hydrocarbons are tailored to a specific need through the choice of the feed paraffinic hydrocarbon and feed aromatic hydrocarbon. An example of this integrated process which has achieved widespread commercial success is the production of linear alkylbenzenes suitable for use in the production of detergent. These alkylated benzenes are often referred to in the art as detergent alkylate and the process is referred to as a detergent alkylation process. It is known to those skilled in the art that these processes currently generate a small but significant amount of undesired by-product hydrocarbons, which normally have a higher molecular weight and higher boiling point than the desired alkylbenzene. These undesired by-products are normally separated from the linear alkylbenzenes in the product recovery zone and concentrated into a stream referred to generically as heavy alkylate. Some of these heavy hydrocarbons, due to their greater solubility in HF acid, are also removed from the process as HF regenerator bottoms stream, sometimes known as polymer or acid soluble oils.

It is an objective of the subject invention to reduce the amount of heavy alkylate and HF regenerator bottoms which is produced in an integrated detergent alkylation process. It is a further objective of the subject invention to improve the quality of the detergent alkylate produced in such an integrated process by reducing the production of undesired by-products which fall within the boiling point range of the desired alkylaromatic hydrocarbons.

There are two feed hydrocarbons consumed in the subject process. These feed hydrocarbons are a paraffin hydrocarbon and an aromatic hydrocarbon. The paraffinic hydrocarbon is preferably a straight chain (unbranched) or normal paraffinic hydrocarbon having from 6 to 22 carbon atoms per molecule. A better quality detergent precursor normally results from the use of olefinic hydrocarbons having from about 10 to 15 carbon atoms per molecule. It is therefore preferred that the feed paraffinic hydrocarbon is a $C_{10}$ to $C_{15}$ paraffin. The feed paraffinic hydrocarbon is normally charged to the process as a mixture of paraffins having different carbon numbers. A preferred method for the production of the paraffinic hydrocarbons is the extraction of straight chain hydrocarbons from a hydrotreated kerosene boiling range petroleum fraction. In other applications of the subject process, it may be preferred to charge a branched paraffinic hydrocarbon. These branched chain paraffins can be obtained by extraction or by suitable oligomerization and treatment processes. The aromatic hydrocarbon which is alkylated in the subject process is preferably benzene, but a higher molecular weight aromatic hydrocarbon may also be charged to the process. The feed aromatic hydrocarbon may therefore be toluene, a xylene, ethylbenzene, phenol, naphthalene, etc.

In the subject process, the feed paraffinic hydrocarbons are first converted to olefinic hydrocarbons in a dehydrogenation zone. The unseparated paraffin/olefin mixture produced as the effluent of the dehydrogenation zone is then passed into the alkylation zone as the olefin-containing feed stream. This is basically because of the high cost of separating olefins and paraffins of the same carbon number, but the presence of the paraffins can also be beneficial as by decreasing the overall olefin concentration in the alkylation reactor and acting as a heat sink for the heat of reaction. The olefin-containing feed stream charged to the alkylation zone may therefore contain from about 30 to about 92 mole percent straight chain paraffins having the same number of carbon atoms per molecule as the olefinic hydrocarbon. These relatively non-reactive paraffins pass through the alkylation zone in various hydrocarbon phase streams and are eventually separated from the alkylate by fractionation and then recycled to the dehydrogenation zone.

It has now been found that the objectives set forth above can be achieved through modification of the dehydrogenation section of the integrated process. This modification comprises the selective hydrogenation of diolefinic hydrocarbons produced in the dehydrogenation reactor. This selective hydrogenation converts at least a substantial amount of the diolefinic hydrocarbons to monoolefinic hydrocarbons, which are the desired product of the dehydrogenation section. At the same time, the concentration of undesired diolefinic hydrocarbons in the net effluent of the dehydrogenation section of the process is decreased. The lower concentration of diolefinic hydrocarbons in the alkylation zone results in a reduced production of by-products including oligomers and biphenyl hydrocarbons. It also is expected to produce a decrease in the consumption of the preferred HF alkylation catalyst. It has also been found that equipment required to perform the selective hydrogenation can be minimized by performing the hydrogenation step just downstream of the customary vapor-liquid or product separator of the dehydrogenation zone. This provides a low cost and facile method of performing the hydrogenation.

It is believed that heretofore attempts to improve the selectivity or product quality of detergent alkylation processes have concentrated on improvements within the alkylation zone itself. These improvements were in such areas as promoting a better or more uniform admixture and contacting of the various hydrocarbon phases with the alkylation catalyst, the optimization of such alkylation conditions as temperature, pressure, and concentrations, the use of additives and modifiers within the alkylation catalyst, etc.

For purposes of discussion, the subject integrated process may be divided into a dehydrogenation section and an alkylation section. The dehydrogenation section will preferably be configured substantially in the manner shown in the drawing. In this arrangement, a fresh paraffinic hydrocarbon feed stream is combined with recycled hydrogen and recycled unconverted hydrocarbons from the alkylation section. This forms the reactant stream which is heated and is then passed through a bed of a suitable catalyst maintained at the proper dehydrogenation conditions of temperature, pressure, etc. The effluent of this catalyst bed or reactor effluent stream is cooled and partially condensed. Part of the uncondensed material is employed as the hydrogen-rich recycle gas stream. The remainder of the uncondensed hydrogen-rich material is the net production of hydrogen which may be used in other applications such as desulfurization. As used herein, the term "rich" is intended to indicate a molar concentration of the indicated compound or class of compounds above 50%. The separation zone also produces a liquid stream referred to herein as the liquid phase process stream. This stream is basically an admixture of dehydrogenated and undehydrogenated acyclic hydrocarbons. This liquid phase stream will also contain some dissolved hydrogen and light hydrocarbons produced by various cracking reactions which occur at the high temperatures employed in the dehydrogenation reactor.

In the subject process, the liquid phase process stream withdrawn from this separation zone is passed into a selective hydrogenation reaction zone. This zone contains a selective hydrogenation catalyst and is maintained at conditions necessary for selective hydrogenation of diolefins to monoolefins. The placement of the selective hydrogenation zone at this point makes it very simple and therefore very economical to perform the desired selective hydrogenation. One reason for this is that the reactants are in the desired liquid phase state as they leave the separation zone. A second reason is that the temperature of the liquid phase process stream as it leaves the separation zone will normally be within the desired operating range of the selective hydrogenation reaction zone. This location for the hydrogenation zone is also preferred since it allows the effluent of the hydrogenation zone to be stripped of hydrogen in the stripping column already employed for the removal of light ends from the liquid phase process stream. This stripping column is therefore also employed in the subject process to ensure that no hydrogen enters the downstream alkylation zone. When the preferred alkylation catalyst is employed, it is highly undesirable to admit hydrogen into the alkylation zone, since it would be necessary to vent this hydrogen from the alkylation zone and it would therefore be necessary to treat the vented hydrogen stream for the removal of vapor phase HF. A relatively minor advantage to this process flow is that it allows at least partial utilization of the small amount of hydrogen dissolved in the liquid in the hydrogenation step. This reduces the required hydrogen addition rate. It also increases the percentage of evolved hydrogen available in the rich separator gas as compared to the stripper off-gas.

The selective hydrogenation conditions employed in the hydrogenation zone are preferably similar to that maintained in the vapor-liquid separation zone of the prior art processes. More specifically, the minimum pressure should be sufficient to maintain the reactants as liquid phase hydrocarbons. A broad range of suitable operating pressures therefore extends from about 40 to about 1000 psig, with a pressure between about 50 and 300 psig being preferred. A relatively moderate temperature between about 25° and 250° C. is preferred. More preferably, the hydrogenation zone is maintained at a temperature between about 50° and about 80° C. The liquid hourly space velocity of the reactants through the selective hydrogenation zone should be above 1.0. Preferably, it is above 5.0 and more preferably it is between 5.0 and 35 hr.$^{-1}$. The optimum set of conditions will of course vary depending on such factors as the composition of the feed stream and the activity and stability of the hydrogenation catalyst.

Another operating condition which may vary depending on catalyst is the ratio of hydrogen to diolefinic hydrocarbons maintained within the selective hydrogenation zone. Some catalysts, such as a palladium on alumina catalyst which was tested, require a higher hydrogen concentration to achieve the desired degree of hydrogenation. Therefore, with some catalysts such as the palladium catalysts, it may be desired to operate with a hydrogen to diolefinic hydrocarbon mole ratio of between 2:1 and 5:1. With this catalyst, it was determined that hydrogen concentrations above this range resulted in the saturation of a significant amount of monoolefinic hydrocarbons. This of course is undesirable as it reduces the yield of the process. With the preferred nickel sulfide catalyst, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the selective hydrogenation zone is maintained between 1:1 and 1.8:1. In some instances, it may be desirable to operate with a less than stoichiometrically required amount of hydrogen, with mole ratios down to 0.75:1 being acceptable.

The selective hydrogenation zone preferably comprises a single fixed bed reactor containing a cylindrical bed of catalyst through which the reactants move in a vertical direction. Contrary to the drawing, it is preferred that the reactants flow upward through the reactor as this provides good mixing. The catalyst may be present as pellets, spheres, extrudates, irregular shaped granules, etc. The prior art suggests the use of a number of metals on the selective hydrogenation catalyst including tungsten, palladium, silver, molybdenum, and nickel. Of these catalysts, it is preferred that the active catalytic metal component present in the hydrogenation catalyst is either nickel or palladium, with nickel being especially preferred. When non-noble metals are employed, the catalyst should have a high concentration or loading of the active metal, with the metal component preferably comprising over 10 wt. % of the catalytic composite. More preferably, over 20 wt. % of the catalytic composite is metallic. It is very highly preferred that the selective hydrogenation catalyst also comprises a sulfur component. The preferred catalyst may therefore be described as a sulfided high nickel catalyst. The preparation of catalysts of this nature is described in U.S. Pat. No. 3,919,341. The preferred selective hydrogenation catalyst has a lower sulfur concentration than the catalyst described in this reference, with sulfur levels between about 0.1 and 0.4 wt. % being preferred. The basic function of the sulfur component is believed to be the attenuation of the hydrogenation activity of the nickel. It is known in the art that carbon monoxide may be passed into a selective hydrogenation reactor for the purpose of noderating or attenuating the hydrogenation reaction. The use of carbon monoxide and other such aoderators though not necessary aay be employed.

The selective hydrogenation catalyst also comprises a support or carrier material which should be relatively inert and refractory to the conditions employed within the process. The support can be formed from a variety of porous materials including various clays, diatomaceous earth, aluminas, ceramics, attapulgus clay, and other synthetically prepared or naturally occurring silicates, kaolin, kieselguhr, titania, alumina, crystalline aluminosilicates, and admixtures of two or more of these materials. The especially preferred carrier material is an alumina. Of the aluminas, gamma-alumina is preferred. The carrier material or support aay have an apparent bulk density of about 0.3 to about 0.8 g/cc, a surface area of about 50 to about 550 m$^2$/g, and a pore volume of between about 0.1 and about 1.0 ml/g.

The effluent of the selective hydrogenation zone is a liquid phase stream similar in nature to the liquid phase process stream removed from the separator but having a reduced concentration of diolefinic hydrocarbons and a corresponding increase in the concentration of monoolefinic hydrocarbons. This effluent stream is passed into a stripping column designed and operated to remove all compounds which are more volatile than the lightest normal hydrocarbon which it is desired to charge to the alkylation section of the integrated process. These lighter materials will be concentrated into a net overhead stream which will comprise an admixture of hydrogen and light hydrocarbons. The purpose of the stripping operation is to prevent the entrance of light volatile materials into the alkylation zone where they would present certain operational problems and also to eliminate the light hydrocarbons from the recycle stream which returns paraffinic hydrocarbons to the dehydrogenation zone. The passage of light monoolefins into the alkylation zone would also lead to the production of an increased aaount of undesired side products through alkylation and polymerization reactions.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts are comprised of a platinum group component supported on a porous carrier material. The preferred carrier material is a refractory inorganic oxide such as gamma-alumina. The preferred dehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkaline earth component. The platinum group component may be chosen from the group consisting of platinum, palladium, rhodium, ruthenium, osmium, and iridium, but platinum is highly preferred. The alkali or alkaline earth component may be selected from the group consisting of the alkali metals—cesium, rubidium, potassium, sodium, and lithium; and the alkaline earth metals—calcium, strontium, barium, and magnesium. This component is preferably either lithium or potassium, with lithium being especially preferred. Another example of a suitable dehydrogenation catalyst is a catalyst which in addition to the previously described platinum and alkali or alkaline earth metal components contains a tin component. This catalytic composite would contain from about 0.1 to about 1 wt. % tin. Yet another catalytic composite which should be highly suited for use in the subject process comprises an indium component in addition to the platinum, tin, and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

A preferred embodiment of the invention may accordingly be characterized as a process for the production of alkylbenzenes which comprises the steps of passing a paraffin feed stream which comprises at least one $C_{10}$-plus linear paraffinic hydrocarbon through a dehydrogenation reaction zone and forming a vapor phase dehydrogenation reaction zone effluent stream which comprises a mixture of hydrogen, mono- and diolefinic $C_{10}$-plus linear hydrocarbons, and $C_{10}$-plus linear paraffins; separating hydrogen from the dehydrogenation reaction zone effluent stream by partially condensing the dehydrogenation reaction zone effluent stream and separating the resultant two-phase admixture in a vapor-liquid separation zone and forming a vapor phase stream which is rich in hydrogen and a liquid phase process stream comprising $C_{10}$-plus linear paraffins, dissolved hydrogen, and mono- and diolefinic $C_{10}$-plus linear hydrocarbons; passing the liquid phase process stream through a selective hydrogenation zone maintained at diolefin selective hydrogenation conditions and in which the liquid phase process stream is contacted with a solid selective hydrogenation catalyst and thereby forming a hydrogenation zone effluent stream which contains less than 0.4 mole percent $C_{10}$-plus diolefinic hydrocarbons; removing substantially all free hydrogen and $C_6$-minus hydrocarbons from the hydrogenation zone effluent stream by passing the hydrogenation zone effluent stream into a light ends stripping column, and producing a stripping column bottoms stream which comprises a mixture of $C_{10}$-plus monoolefinic linear hydrocarbons and $C_{10}$-plus linear paraffins; contacting the stripping column bottoms stream with an alkylation catalyst and with benzene within an alkylation zone maintained at alkylation-promoting conditions, and producing an alkylation zone effluent stream which comprises $C_{10}$-plus linear paraffins and alkylbenzenes, and recovering the alkylbenzenes from the alkylation zone effluent stream.

The net effluent of the dehydrogenation section is passed into an alkylation section, which comprises an alkylation zone and a fractionation or alkylate recovery zone. The alkylation zone can have a number of different configurations depending on the catalyst and reactor vessels which are employed. A solid alkylation catalyst could be employed in the alkylation zone. For example, one current trend in heterogeneous alkylation catalysts is the use of a zeolitic catalyst as described in U.S. Pat. Nos. 3,751,506; 4,387,259; and 4,409,412. The use of a homogeneous mineral acid catalyst is however greatly preferred, with liquid phase HF being especially preferred.

Chemical reactions which involve olefinic hydrocarbons and are catalyzed by hydrogen fluoride usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The alkylation zone preferably has an overall arrangement similar to that shown in previously referred to U.S. Pat. No. 3,494,971. An improvement to this is shown in U.S. Pat. No. 4,225,737. In this arrangement, the two feed hydrocarbon streams and liquid phase HF are charged to a reactor. The effluent of this reactor is passed into a first settling zone and separated into HF and hydrocarbon phases. The settling zones are preferably elongated horizontal vessels. The HF is withdrawn and divided into a first portion passed into the HF regeneration column for regeneration and a second portion returned to the reactor. The hydrocarbon phase is withdrawn from the first settling zone and charged to a contactor, which is sometimes referred to as the second "reactor", as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as an alkylation zone effluent stream but is preferably passed into a stripping column in which dissolved HF is removed overhead and some of the feed aromatic hydrocarbon is also recovered. The net bottoms of this HF stripping column is charged to the fractionation or other product recovery zone employed in the process. It may be desirable to depart from these preferences and employ more than one reactor.

The alkylation reactor and the contactor are maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about −20° to about 95° C., but the reaction is preferably conducted at a temperature of from 15° to 50° C. The volumetric ratio of HF to the total amount of hydrocarbons entering the reactor should be maintained within the broad range of from about 0.2:1 to about 10:1. A preferred range for this ratio is from 1:1 to 2.5:1. To lessen the production of polyalkylated benzenes and to reduce the amount of olefin polymerization in the reactor, the mole ratio of benzene to the monoolefin at the point of initial olefin-acid contact is maintained above 1:1, but preferably below 10:1. A range of typical commercial ratios is from 3:1 to about 8:1.

The conditions maintained within the contactor are similar to the conditions maintained in the reactor, but some adjustment is required. For instance, since essentially all of the olefin is preferably consumed in the reactor, the hydrocarbon stream fed to the contactor is substantially free of olefins. There is therefore no benzene to olefin ratio to be specified. The same pressure range may be used in the contactor as in the reactor, but a higher temperature is preferred. This higher temperature should be at least 6 to 10 Centigrade degrees above that used in the reactor. All temperatures specified herein are intended to refer to the average temperature of the liquid stream entering the respective zone.

The HF/hydrocarbon ratio maintained in the contactor will normally be slightly lower, and a typical ratio is about 1:1. The purity of acid used in the contactor will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contactor. The recycle acid for use in the reactor is withdrawn from the second settling zone and therefore contains a higher concentration of high molecular weight hydrocarbonaceous impurities. The acid used in the reactor preferably contains about 85-92 wt. % HF and will typically be about 90 wt. % HF. The acid used in the contactor preferably contains more than 90 wt. % HF and is typically about 93-94 wt. % HF.

The effluent streams leaving the reactor and the contactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into quiescent settling zones. The two settling zones will normally be maintained at a temperature which is set by the entering HF-hydrocarbon mixtures withdrawn from the respective upstream vessels. They will therefore be at substantially the same temperature as the immediately upstream reaction or contacting zone. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 90 seconds but less than 30 minutes.

The hydrocarbonaceous phase removed from the second settling zone is preferably passed into a fractionation column commonly referred to as the HF stripping column. This column derives its name from its basic function in the prior art of preventing the passage of HF into the downstream fractionation zone. Representative conditions for the operation of the HF stripping column include an overhead vapor temperature of about 250° F. at a pressure of approximately 36 psig. There is normally no external reflux to this column. The overhead vapor stream of the HF stripping column is normally completely condensed by cooling it to about 100° F. or less and is then decanted and recirculated as described above. The entire hydrocarbonaceous effluent of the second settling zone is normally passed onto the top tray of this column. The net bottoms stream of this column contains the product alkylate.

Fractionation systems and conditions suitable for use as an effective separation zone to recover the product alkylate from the bottoms stream of the HF stripping column are described in U.S. Pat. Nos. 3,950,448; 4,237,327; and 4,237,328. For instance, the bottoms stream of the HF stripping column is preferably passed into a second fractionation column referred to as a benzene column. The benzene column is operated under conditions effective to cause the division of the entering hydrocarbons into a high purity benzene stream which is removed as the overhead liquid and a bottoms stream containing the alkylate product. This bottoms stream is passed into a third fractionation column referred to as a paraffin column. The non-reactive paraffins are removed as an overhead liquid stream. The bottoms stream of the third fractionation column comprises the product alkylate and any higher molecular weight side product hydrocarbons formed in the reaction zone. This bottoms stream is passed into a fourth fractionation column which produces a high purity overhead stream containing the detergent alkylate. A bottoms stream comprising polymerized olefins and polyalkylated benzenes (heavy alkylate) is removed from the fourth column for disposal. The third and the fourth fractionation columns are normally operated at a subatmospheric pressure. An alternative method of performing this separation is disclosed in previously cited U.S. Pat. No. 3,950,448. In this arrangement, the bottoms stream of the HF stripping column is passed into a column referred to as a paraffin column. All of the feed aromatic hydrocarbon is withdrawn from the HF stripping column in an overhead stream or as a liquid stream removed below a contact condenser located in the top of the column. The net bottoms stream of the HF stripping column is therefore devoid of the feed aromatic hydrocarbon. This bottoms stream is then separated in the same manner as set out above.

I claim as my invention:

1. A detergent alkylation process for the production of an alkylaromatic hydrocarbon by the reaction of an aromatic hydrocarbon with monoolefinic hydrocarbons in the presence of paraffinic hydrocarbons and in the substantial absence of diolefinic hydrocarbons which comprises:
   (a) passing a $C_6$–$C_{22}$ paraffinic hydrocarbon through a dehydrogenation reaction zone maintained at dehydrogenation conditions effective to produce a vapor phase dehydrogenation reactor effluent stream comprising
      (i) $C_6$-minus light hydrocarbons
      (ii) $C_6$–$C_{22}$ paraffinic hydrocarbons
      (iii) $C_6$–$C_{22}$ monoolefinic hydrocarbons
      (iv) $C_6$–$C_{22}$ diolefinic hydrocarbons and
      (v) hydrogen;
   (b) cooling and partially condensing said dehydrogenation reactor zone effluent to form a vapor-liquid dehydrogenation reactor zone effluent;
   (c) passing said vapor-liquid dehydrogenation reactor zone effluent to a vapor-liquid separation zone to separate said vapor-liquid dehydrogenation reactor effluent stream into a vapor phase process stream comprising hydrogen and a liquid phase process stream which comprises:
      (i) dissolved hydrogen
      (ii) $C_6$-minus light hydrocarbons
      (iii) $C_6$–$C_{22}$ diolefinic hydrocarbons;
      (iv) $C_6$–$C_{22}$ diolefin hydrocarbons;
   (d) passing said liquid phase process stream derived from said vapor-liquid separtion zone and a controlled amount of a hydrogen feed stream through a selective hydrogenation reaction zone located downstream of said vapor-liquid separation zone and upstream of a hereinafter defined stripping zone of step (e), said selective hydrogenation zone containing a selective hydrogenation catalyst and maintained at selective hydrogenation conditions, wherein said amount of hydrogen in said hydrogen feed stream is selected to convert substantially all of said $C_6$–$C_{22}$ diolefin to the corresponding monoolefinic hydrocarbon and to produce a hydrogenation reaction zone effluent stream substantially free of $C_6$–$C_{22}$ diolefinic hydrocarbons and comprising
      (i) hydrogen
      (ii) dissolved $C_6$-minus light hydrocarbons
      (iii) $C_6$–$C_{22}$ paraffinic hydrocarbons; and
      (iv) $C_6$–$C_{22}$ monoolefinic hydrocarbons;
   (e) passing said hydrogenation reaction zone effluent stream into a stripping zone operated at conditions to selectively separate and remove hydrogen and $C_6$-minus light hydrocarbons from said hydrogenation effluent stream and to produce a stripping zone bottom effluent stream comprising:
      (i) $C_6$–$C_{22}$ paraffinic hydrocarbons and
      (ii) $C_6$–$C_{22}$ monoolefinic hydrocarbons;
   (f) passing said stripping zone bottoms effluent stream and an aromatic hydrocarbon into an alkylation zone maintained at alkylation-promoting conditions and containing an alkylation zone catalyst to alkylate said aromatic hydrocarbon and to produce an alkylation zone effluent stream comprising:
      (i) alkylaromatic hydrocarbon; and
      (ii) $C_6$–$C_{22}$ paraffinic hydrocarbon; and
   (g) recovering said alkylaromatic hydrocarbon from said alkylation zone as the product of said detergent alkylate process.

2. The process of claim 1 further characterized in that the selective hydrogenation conditions include the presence of less than 2.0 times the stoichiometrically required amount of hydrogen for the selective hydrogenation of said $C_6$–$C_{22}$ diolefinic hydrocarbons present in the liquid phase process stream to the corresponding $C_6$–$C_{22}$ monoolefinic hydrocarbons.

3. The process of claim 2 further characterized in that the mole ratio of hydrogen to $C_6$–$C_{22}$ diolefinic hydrocarbons in the liquid phase process stream is maintained between 1.0:1.0 and 1.8:1.0.

4. The process of claim 3 further characterized in that the aromatic hydrocarbon is benzene.

5. The process of claim 4 further characterized in that said $C_6$–$C_{22}$ paraffinic hydrocarbons in said alkylation zone effluent stream are recovered from said alkylation zone effluent stream and recycled to said dehydrogenation reaction zone.

6. The process of claim 3 further characterized in that the selective diolefin hydrogenation catalyst comprises palladium and a refractory inorganic support material.

7. The process of claim 3 further characterized in that the selective diolefin hydrogenation catalyst comprises nickel and sulfur and an inorganic refractory support material.

8. A detergent alkylation process for the production of linear alkylbenzenes by the reaction of benzene with $C_{10}$-plus linear monoolefinic hydrocarbons in the presence of $C_{10}$-plus linear paraffinic hydrocarbons and less than 0.4 mole percent $C_{10}$-plus diolefinic hydrocarbon which comprises:
   (a) passing a paraffinic hydrocarbon feed stream which comprises at least one $C_{10}$-plus linear paraffinic hydrocarbon through a dehydrogenation reaction zone maintained at dehydrogenation conditions effective to produce a vapor phase dehydrogenation reactor effluent stream comprising:
      (i) $C_{10}$-plus linear paraffinic hydrocarbons;
      (ii) $C_{10}$-plus linear monoolefinic hydrocarbons;
      (iii) $C_{10}$-plus linear diolefinic hydrocarbons;
      (iv) $C_{10}$-minus light hydrocarbon by-products; and
      (v) hydrogen
   (b) cooling and partially condensing said dehydrogenation reactor zone effluent to form a vapor-liquid dehydrogenation reactor zone effluent;
   (c) passing said vapor-liquid dehydrogenation reactor zone effluent to a vapor-liquid separation zone to separate said vapor-liquid dehydrogenation reactor effluent stream into a vapor phase process stream comprising hydrogen and a liquid phase process stream which comprises:
      (i) dissolved hydrogen;
      (ii) $C_{10}$-minus light hydrocarbon by-products;
      (iii) $C_{10}$-plus paraffinic hydrocarbons;
      (iv) $C_{10}$-plus monoolefinic hydrocarbons; and
      (v) $C_{10}$-plus diolefinic hydrocarbons;
   (d) passing said liquid phase process stream derived from said vapor-liquid separation zone and a controlled amount of a hydrogen feed stream through a selective hydrogenation reaction zone located downstream of said vapor-liquid separation zone and upstream of a hereinafter defined stripping zone of step (e), said selective hydrogenation zone containing a selective hydrogenation catalyst and maintained at selective hydrogenation conditions wherein said amount of hydrogen in said hydrogen feed stream is selected to convert said $C_{10}$-plus diolefinic hydrocarbons to the corresponding $C_{10}$-plus monoolefinic hydrocarbon to provide a hydrogenation reaction zone effluent containing less than 0.4 mole percent $C_{10}$-plus diolefinic hydrocarbons and comprising:
  (i) hydrogen
  (ii) dissolved $C_{10}$-minus light hydrocarbon by-products
  (iii) $C_{10}$-plus paraffinic hydrocarbons; and
  (iv) $C_{10}$-plus monoolefinic hydrocarbons
(e) passing said hydrogenation reaction zone effluent stream into a stripping zone operated at conditions to selectively separate and remove said hydrogen and said $C_{10}$-minus light hydrocarbon by-products from said hydrogenation reaction zone and to produce a stripping zone bottoms stream comprising:
  (i) $C_{10}$-plus paraffinic hydrocarbons and
  (ii) $C_{10}$-plus monoolefinic hydrocarbons;
(f) passing said stripper zone bottoms effluent stream and benzene into an alkylation zone maintained at alkylation promotion conditions to produce an alkylation zone effluent stream comprising
  (i) $C_{10}$-plus paraffinic hydrocarbon and
  (ii) a linear alkylbenzene; and
(g) recovering said linear alkylbenzenes from said alkylation zone effluent stream.

9. The process of claim 8 further characterized in that the alkylation catalyst comprises HF.

10. The process of claim 9 further characterized in that the paraffin feed stream comprises a mixture of $C_{15}$ to $C_{20}$ linear paraffinic hydrocarbons.

11. The process of claim 9 further characterized in that the paraffin feed stream comprises $C_{10}$ to $C_{15}$ linear paraffinic hydrocarbons.

12. The process of claim 11 further characterized in that said $C_{10}$-plus linear paraffinic hydrocarbons are recovered from said alkylation zone effluent stream and are recycled to said dehydrogenation reaction zone.

13. The process of claim 12 further characterized in that the hydrogenation catalyst comprises nickel, sulfur, and a refractory inorganic support.

14. The process of claim 12 further characterized in that the hydrogenation catalyst comprises palladium and a refractory inorganic support.

* * * * *